United States Patent
Biguet et al.

(10) Patent No.: US 9,353,192 B2
(45) Date of Patent: May 31, 2016

(54) METHOD FOR PURIFYING GLUCOSE POLYMERS FOR PERITONEAL DIALYSIS SOLUTIONS

(75) Inventors: Marc Biguet, Neuve Chapelle (FR); Stéphane Bourdain, Bethune (FR); Pierrick Duflot, La Couture (FR)

(73) Assignee: ROQUETTE FRERES, Lestrem (FR)

( * ) Notice: Subject to any disclaimer, the term of this patent is extended or adjusted under 35 U.S.C. 154(b) by 907 days.

(21) Appl. No.: 13/266,820

(22) PCT Filed: Apr. 29, 2010

(86) PCT No.: PCT/FR2010/050815
§ 371 (c)(1), (2), (4) Date: Oct. 28, 2011

(87) PCT Pub. No.: WO2010/125315
PCT Pub. Date: Nov. 4, 2010

(65) Prior Publication Data
US 2012/0046460 A1 Feb. 23, 2012

(30) Foreign Application Priority Data
Apr. 30, 2009 (FR) ..................................... 09 52879

(51) Int. Cl.
| | | |
|---|---|---|
| *C12P 19/04* | (2006.01) | |
| *A61M 1/28* | (2006.01) | |
| *C12P 19/14* | (2006.01) | |
| *C08B 30/18* | (2006.01) | |
| *A61L 2/00* | (2006.01) | |
| *B01D 61/14* | (2006.01) | |
| *B08B 9/08* | (2006.01) | |
| *C11D 11/00* | (2006.01) | |

(52) U.S. Cl.
CPC ............... *C08B 30/18* (2013.01); *A61L 2/0017* (2013.01); *A61L 2/0023* (2013.01); *B01D 61/145* (2013.01); *B08B 9/08* (2013.01); *C11D 11/0041* (2013.01); *C11D 11/0064* (2013.01); *C12P 19/04* (2013.01); *C12P 19/14* (2013.01); *A61M 1/287* (2013.01)

(58) Field of Classification Search
CPC ............................ C12P 19/04; A23G 2200/06
USPC ........................................................ 536/127
See application file for complete search history.

(56) References Cited

U.S. PATENT DOCUMENTS

| | | | | |
|---|---|---|---|---|
| 3,238,064 | A * | 3/1966 | Celestian et al. | 127/69 |
| 3,793,461 | A * | 2/1974 | Yuen | 514/53 |
| 3,928,135 | A | 12/1975 | Milner | |
| 4,182,756 | A * | 1/1980 | Ramsay et al. | 514/54 |
| 4,294,623 | A * | 10/1981 | Hidaka et al. | 127/55 |
| 4,683,198 | A * | 7/1987 | Ishikawa et al. | 435/22 |
| 5,626,751 | A * | 5/1997 | Kikuchi et al. | 210/321.75 |
| 6,046,160 | A * | 4/2000 | Obi-Tabot | 514/9.4 |
| 6,284,140 | B1 * | 9/2001 | Sommermeyer | A61K 31/715 210/646 |
| 6,630,586 | B1 | 10/2003 | Fouache et al. | |
| 6,706,251 | B1 * | 3/2004 | Zabel et al. | 424/1.29 |
| 6,770,148 | B1 * | 8/2004 | Naggi et al. | 127/71 |
| 6,861,519 | B2 * | 3/2005 | Backer et al. | 536/102 |
| 8,933,219 | B2 * | 1/2015 | Duflot | C08B 30/04 127/71 |
| 8,999,693 | B2 * | 4/2015 | Fukuda | 435/200 |
| 2004/0014961 | A1 | 1/2004 | Backer et al. | |
| 2004/0194810 | A1 | 10/2004 | Strothoff et al. | |
| 2005/0142167 | A1 | 6/2005 | Backer et al. | |
| 2008/0105282 | A1 | 5/2008 | Fernholz et al. | |

FOREIGN PATENT DOCUMENTS

| | | | |
|---|---|---|---|
| CA | 2142528 | 8/1995 | |
| CA | 2088933 C * | 5/1998 | A23L 1/095 |
| EP | 0 667 356 | 8/1995 | |
| EP | 1 006 128 | 6/2000 | |
| EP | 1 108 434 | 6/2001 | |
| EP | 1 369 432 | 12/2003 | |
| WO | WO 97/02753 | 1/1997 | |
| WO | WO 2005/102546 | 11/2005 | |

OTHER PUBLICATIONS

Written Opinion in International Application No. PCT/FR2010/050815, Oct. 12, 2010, pp. 1-12.

* cited by examiner

*Primary Examiner* — Patrick Lewis
*Assistant Examiner* — Everett White
(74) *Attorney, Agent, or Firm* — Saliwanchik, Lloyd & Eisenschenk

(57) ABSTRACT

The invention relates to a method of purifying glucose polymers for the production of peritoneal dialysis solutions, characterized in that it includes at least one step of processing activated carbon and/or granular black, at least one sterilizing filtration step, at least one heat treatment step, and at least one ultrafiltration step.

6 Claims, No Drawings

METHOD FOR PURIFYING GLUCOSE POLYMERS FOR PERITONEAL DIALYSIS SOLUTIONS

CROSS-REFERENCE TO RELATED APPLICATION

This application is the U.S. national stage application of International Patent Application No. PCT/FR2010/050815, filed Apr. 29, 2010, the disclosure of which is hereby incorporated by reference in its entireties, including all figures, tables and amino acid or nucleic acid sequences.

The present invention relates to a method for purifying glucose polymers for the production of peritoneal dialysis solutions.

Peritoneal dialysis is a type of dialysis of which the objective is to remove waste such as urea, creatinine, excess potassium or surplus water that the kidneys do not or no longer manage to purify from the blood plasma. This medical treatment is indicated in the case of terminal chronic renal failure.

Peritoneal dialysis uses two principles, put into action by virtue of the physiological property of permeability of the peritoneum: the ultrafiltration of liquid and the purification of waste by diffusion.

The peritoneum is a serous membrane, with a surface area of approximately 2 m², composed of two sheets: the parietal sheet lining the internal face of the walls (abdomen, lesser pelvis, diaphragm) and the visceral sheet surrounding the organs. There is a very high blood flow into the peritoneum owing to the large number of blood vessels and capillaries, in particular in the parietal sheet. The surface area of the vascular network represents approximately 1 m². Housed between the two sheets is a virtual space: the peritoneal cavity. In order to perform dialysis, an artificial liquid, the dialysate, is introduced into the peritoneal cavity. This liquid will subsequently be evacuated after a predetermined contact time.

The dialysates most commonly used are composed of a buffer solution (of lactate or of bicarbonate) at acidic pH (5.2-5.5) or physiological pH (7.4) to which are added electrolytes (sodium, calcium, magnesium, chlorine) and an osmotic agent (glucose or a glucose polymer, such as "icodextrin" present in the ambulatory peritoneal dialysis solution "EXTRANEAL® sold by the company BAXTER).

The electrolytes and the osmotic agent each play a role in the exchange mechanism, according to their respective physicochemical properties:

metabolic waste (such as urea or creatinine) or other overabundant electrolytes that the kidney no longer or insufficiently removes via the urinary tract and the urine will be extracted from the blood plasma by diffusion of the components toward the dialysate, of which the concentration levels of these same components are lower;

the surplus water, that the kidney normally removes in order to regulate plasma volume, will be attracted by osmolarity; this process is called ultrafiltration; the rate of ultrafiltration varies according to the concentration of glucose or glucose polymer in the dialysate: the more concentrated the solution is, the more the water present in the body will be taken up by the dialysate.

However, although glucose has the advantage of being relatively safe and inexpensive, it has a certain number of drawbacks. Owing to its small size, the glucose rapidly crossing the peritoneum leads to a loss of osmotic gradient and to a loss of ultrafiltration in 2 to 4 hours of infusion.

Moreover, the daily introduction of the dialysate can in the long-term cause a risk of detrimental modification of the peritoneal membrane, restricting the use of this method for a limited period over time, generally between two and ten years.

The catheter implanted in the peritoneal cavity is a point of entry conducive to microorganisms. The numerous occasions on which the catheter is handled during the infusion and drainage phases increase the risk of local or general infection.

It has been suggested that the ultrafiltration characteristics of peritoneal dialysis solutions could be better by replacing the glucose with high-molecular-weight substances, such as glucose polymers.

Standard glucose polymers are produced by acid or enzymatic hydrolysis of cereal starch or tuberous plant starch.

The acid hydrolysis of starch, which is completely random, or the slightly more ordered enzymatic hydrolysis thereof, provide mixtures of glucose and of glucose polymers which comprise very short molecules, having a low degree of polymerization (or D.P.), and also very long molecules, having a high D.P. Glucose polymers thus have an extremely varied molecular weight.

In the more particular field of the use of glucose polymers for continuous ambulatory peritoneal dialysis, European patent application EP 207 676 teaches that glucose polymers forming clear and colorless solutions at 10% in water, having a weight-average molecular weight (Mw) of 5000 to 100 000 daltons and a number-average molecular weight (Mn) of less than 8000 daltons are preferred.

Such glucose polymers comprise, also preferably, at least 80% of glucose polymers of which the molecular weight is between 5000 and 50 000 daltons, little or no glucose or glucose polymers having a DP less than or equal to 3 (molecular weight 504) and little or no glucose polymers of molecular weight greater than 100 000 (DP of about 600).

In other words, the preferred glucose polymers are glucose polymers with a low polydispersity index (value obtained by calculating the Mw/Mn ratio).

It is in fact easily imagined for this application that low-molecular-weight monomers or polymers rapidly cross the peritoneal wall and are thus of no long-lasting value for creating an osmotic pressure gradient, and that very high-molecular-weight polymers, which lack osmotic power, are to be avoided and even prohibited since they are potentially dangerous if they come to precipitate subsequent to retrogradation thereof.

The methods proposed in this patent application EP 207 676 for obtaining these glucose polymers with a low polydispersity index consist:

either in carrying out a fractional precipitation of a maltodextrin with a water-miscible solvent, or in carrying out a molecular filtration of this same maltodextrin through various membranes possessing an appropriate cut-off or exclusion threshold.

In the two cases, these methods aim to remove at the same time the very high-molecular-weight polymers and the low-molecular-weight monomers or oligomers.

However, these methods do not provide satisfaction both from the point of view of their implementation and from the point of view of the yields and the quality of the products that they make it possible to obtain.

In the interests of developing a method for producing a completely water-soluble starch hydrolyzate with a low polydispersity index preferentially less than 2.5, preferably having an Mn of less than 8000 daltons and having an Mw of between 12 000 and 20 000 daltons, said method being lacking the drawbacks of the prior art, the applicant company endeavor to solve this problem in its patent EP 667 356.

This method consists in:
- subjecting a waxy starch milk to acid hydrolysis to give a DE between 8 and 15;
- optionally adding to this acid hydrolysis by means of an enzymatic hydrolysis with bacterial alpha-amylase to give a DE between 11 and 18;
- chromatographing this acid-enzyme double hydrolyzate on macroporous strong cationic resins in alkali metal or alkaline-earth metal form;
- collecting the starch hydrolyzate excluded during this chromatography step.

In this patent, in order to obtain a starch hydrolyzate having a polydispersity index of less than 2.5, the starch hydrolyzate excluded during this chromatography step is collected in a weight yield of about 60% of the hydrolyzate processed in the chromatography step.

This starch hydrolyzate in question then preferably contains less than 3% of glucose and of glucose polymers having a DP less than or equal to 3 and less than 0.5% of glucose polymers having a DP greater than 600.

It is accepted by experts in the field of peritoneal dialysis that these glucose polymers, used for their osmotic power, are entirely satisfactory.

It nevertheless remains the case that treatment by peritoneal dialysis has a certain number of drawbacks linked to the risks of the method.

One of the major risks is peritonitis.

Clinical suspicion of peritonitis is diagnosed when there is a cloudy dialysate together with variable clinical manifestations, namely abdominal pain, nausea, vomiting, diarrhea and fever.

These episodes of peritonitis are caused by intraperitoneal bacterial infections, and the diagnosis is usually easily established through positive dialysate cultures.

"Sterile peritonitis", which is also described as aseptic, chemical or culture-negative peritonitis, is for its part typically caused by a chemical irritant or a foreign body.

Since the introduction of icodextrin for the preparation of peritoneal dialysis solutions, sporadic cases of aseptic peritonitis have been reported that can be linked to various causes, and in particular induction by pro-inflammatory substances potentially present.

Moreover, the tests described today in the pharmacopeia for detecting pyrogenic substances are the following:
- the test for detecting bacterial endotoxins, majority components of Gram-negative bacteria (LAL test),
- the rabbit pyrogene test.

Although generally reliable, these two tests have their limits.

The rabbit pyrogene test is based on the indirect detection of pyrogenic substances by measuring an elevation in the temperature of the rabbit that has been injected with the product containing these substances (febrile response).

This test can produce false negatives, if the undesirable substance has a biological activity that is too weak or a concentration that is too low to induce a general pyrogenic response.

However, this substance may have a biological activity or concentration sufficient to produce a local inflammatory reaction.

The LAL test, for its part, detects only bacterial endotoxins (LPS) and also β-glucans, which are components of the walls of fungal flora.

The other biological impurities (DNA, etc.) are not detected. The same is true for peptidoglycans, which are majority components of the cell membranes of Gram-positive bacteria.

The manifestation of aseptic peritonitis observed with peritoneal dialysis solutions containing icodextrin therefore, for certain cases, attest to the way that some substances can escape the tests described in the pharmacopeia and can be responsible for undesirable clinical effects.

In order to remedy this situation, the company BAXTER proposes making efforts to detect the Gram-positive microbial contaminants.

In particular, in its patent EP 1 720 999, the company BAXTER proposes developing a method based on the detection of peptidoglycans, which are the major components of Gram-positive bacterial membranes, in particular in glucose polymers for the preparation of peritoneal dialysis solutions.

This method consists in carrying out, on the glucose polymers:
- "bioburden" testing for detecting a particular acidophilic thermophilic Gram-positive microorganism: *Alicyclobacillus acidocaldarius*, then
- sterilization of said glucose polymers, then
- a test consisting in adding a reagent capable of reacting with the peptidoglycans so as to induce a serine protease cascade reaction,
- quantification of said peptidoglycans.

If it is determined that the amount of these peptidoglycans sought in the glucose polymers is less than a certain threshold (10 ng/ml of a 7.5% solution of glucose polymer, i.e. 133 ng/g of glucose polymers), these glucose polymers are then used to prepare the actual peritoneal dialysis solution.

In other words, in order to prevent the occurrence of these episodes of aseptic peritonitis, the company BAXTER proposes, for the production and use of peritoneal dialysis solutions, a protocol for detecting peptidoglycans in the peritoneal dialysis solution.

Moreover, while the upstream treatment of glucose polymers is mentioned in this patent EP 1 720 999, this treatment is only by means of affinity resins capable of trapping the peptidoglycans as such.

It is not therefore envisioned to modify the method for producing glucose polymers in such a way that the final product is free of contamination by acidothermophilic bacteria of *Alicyclobacillus acidocaldarius* type or by membrane debris of these particular bacteria.

Consequently, there is an unsatisfied need to provide, by means of a safe method of preparation and purification, substances for peritoneal dialysis of better quality, in this case glucose polymers, in order to ensure that these substances are effectively free of contaminating substances.

The applicant company has therefore found that this need can be satisfied by implementing a noteworthy purification method, combining a certain number of steps of treatment with activated carbon/granular black carbon, of filtration (microfiltration and ultrafiltration) and of heat treatment organized in a manner suitable for preventing any contamination.

The method for purifying glucose polymers for the production of peritoneal dialysis solutions in accordance with the invention is more particularly characterized in that it comprises:
- at least one step of treatment with activated carbon and/or with granular black carbon,
- at least one sterilizing filtration step,
- at least one heat treatment step, and
- at least one ultrafiltration step.

It is important to note that the combination of these four steps guarantees the virtual absence of contaminants of any nature regardless of their size (e.g. endotoxins, peptidoglycans and β-glucans).

This method is applied to the final glucose polymers for the production of peritoneal dialysis solutions, i.e. those that will be used for the preparation of the dialysis solution.

The secure nature of such a method makes it possible more particularly to limit the bacterial testing at the end of said method to the high-sensitivity peptidoglycan detection test developed and validated by the applicant company (which will be described hereinafter) and to the endotoxin detection test (LAL test).

For the purpose of the invention, the term "virtual absence" is intended to mean a quantification at thresholds well below what is described in the pharmacopeia tests, i.e.:

for endotoxins (and β-glucans) via the LAL test (endpoint gel clot method) using reagents produced by CHARLES RIVER-ENDOSAFE (LAL lysate with a sensitivity of 0.015 E.U/ml ref. OR15015 and CSE endotoxins 500 ng or 10 ng per vial ref. E110 or E120): ≤0.6 EU/g;

for peptidoglucans (and β-glucans) via a high-sensitivity test developed by the applicant company: <8 ng/g of glucose polymers (thus well below the reference threshold described in patent EP 1 720 999 for peptidoglucans).

The expression "high-sensitivity test developed and validated by the applicant company" is intended to mean a test developed and validated by the applicant company by adapting the SLP-HS single reagent set kit ref. 293-58301 produced and sold by the company WAKO Pure Chemical Industries Ltd.

This test consists in adding the reagent termed "SLP-HS" (Silkworm Larvae Plasma-High. Sensitivity) reagent prepared from silkworm plasma, capable of:

reacting with the peptidoglycans and β-glucans contained in a glucose polymer solution prepared at 5% in water (special water for the LAL test for example), inducing a serine protease cascade reaction and detecting and/or quantifying said peptidoglycans and β-glucans by means of a TOXINOMETER tube reader manufactured and sold by the company WAKO Pure Chemical Industries Ltd, at very low thresholds, i.e.:

a limit of detection (LOD) at a threshold of approximately 0.05 ng/ml (i.e. 1 ng/g of glucose polymer) and a limit of quantification (LOQ) at a threshold of approximately 0.15 ng/ml (3 ng/g of glucose polymer)

(LOD and LOQ determined in the glucose polymer product tested).

More specifically, the SLP-HP test consists in preparing the glucose polymer to be tested in solution at 5% in water of suitable quality (special water for the LAL test for example), preparing a calibration range of peptidoglucans in water over the range of application of 0.04 to 2.5 ng/ml (target values) with the peptidoglucan standard (extracted from *Staphylococcus aureus*) of the SLP-HS single reagent set kit in order to establish a calibration straight line (linear regression on the logarithmic scale Ta=f (content of PG)), introducing 100 μl of the prepared solution to be tested into the HS-SLP tube after reconstitution by adding 100 μl of the diluent (supplied in the abovementioned kit), introducing the SLP-HS tube into the incubation well of the TOXINOMETER tube reader (WAKO Pure Chemical Ltd) thermostated at 30° C. and configured according to the conditions recommended by the manufacturer, the PG content of the solution to be tested is calculated by means of the calibration straight line established.

The result is expressed in ng/ml of 5% solution tested then in ng/g of glucose polymer.

It is noteworthy that the amounts of these peptidoglycans/β-glucans ultimately in the glucose polymer obtained by means of the method in accordance with the invention are guaranteed to be much lower than 8 ng/g of glucose polymer, i.e. at least and approximately 16 times below the threshold described in patent EP 1 720 999.

In the method for purifying glucose polymers for peritoneal dialysis, as has been described above, the first of the four means implemented consists in using activated carbon and/or granular black carbon in a particular configuration.

The applicant company recommends implementing this means in at least one of the following three variations:

in a first variation of the method in accordance with the invention: in the case of the use of granular black carbon, this configuration is based on operation in the countercurrent mode.

The residence time in the column is approximately three hours. The percolation is carried out at a rate of about 2 m/h at a temperature of about 80° C. in order to avoid bacterial contamination.

The contact between the starch hydrolyzate to be purified and the granular black carbon takes place in the countercurrent mode in the sense that the starch hydrolyzate to be purified first of all comes into contact with the saturated granular black carbon at the bottom of the column.

The purified starch hydrolyzate is therefore recovered at the top of the column of granular black carbon, at the same time as the purified granular black carbon.

In this way, the final layer of granular black carbon at the top of the column acts as a "safety barrier".

This arrangement can be controlled by carrying out granular black carbon "expelling" operations. The column is stopped, the saturated granular black carbon is withdrawn via the bottom, and is replaced via the top with regenerated granular black, carbon.

The saturated granular black carbon is desugared before being regenerated by heat treatment in a hearth furnace.

At start-up, and for safety, the first $m^3$ of starch hydrolyzate with a low dry matter content are downgraded.

The monitoring of the decrease in the level of contaminants (endotoxins, peptidoglycans and β-glucans) can be analyzed by taking a certain number of samples (five for example) from the bottom of the column to the top;

in a second variation of the method in accordance with the invention: in the case of use of activated carbon, this configuration is based on a "double" treatment with activated carbon.

The starch hydrolyzate entering is mixed with activated carbon (between 0.5% and 1.5% relative to the dry matter to be treated) at, a temperature between 70 and 75° C. for one hour.

The starch hydrolyzate is then filtered and analyzed.

The starch hydrolyzate then undergoes a treatment of the same nature. This second treatment is the "safety" treatment.

The applicant company recommends using activated carbon of different porosity in these two stages, so as to take into account the variability of the size of the contaminants;

in a third variation of the method in accordance with the invention, it is chosen to combine a granular black carbon stage and an activated carbon stage.

The applicant company then recommends placing the column of granular black carbon at the head of this combination.

The conditions for implementing these two stages are in accordance with what is described above.

The second of the four means implemented for purifying the glucose polymers for the production of peritoneal dialysis solutions in accordance with the invention consists in using a sterilizing filtration.

This sterilizing filtration step consists principally of a membrane filtration where the pore diameter is 0.22 μm, preceded, where appropriate, by a membrane prefiltration where the pore diameter is 0.45 μm (thus complying with the "sterility test" as described in the European pharmacopeia—6$^{th}$ edition, chapter 2.6.1. *Sterility*).

This step makes it possible to retain any contamination by microorganisms, and in particular acidothermophilic bacteria of *Alicyclobacillus acidocaldarius* type, their size being greater than the filtration pore diameters.

The filtration is carried out using several cartridge filters inserted into a vertical casing toward which the syrup is directed. These cartridge filters are supplied by the companies PALL or MILLIPORE, for example. The size of the cartridges may be 10, 20 or 30 inches, and the number of cartridges installed makes it possible to obtain a filtration surface area sufficient to pass a product flow rate of between 1 and 20 l/minutes/m².

These cartridge filters have resistance capacities for continuous working at high temperature, of about 75° C., and for passing the abovementioned flow rate for a period of time greater than 700 h.

Working at a temperature above 75° C. makes it possible to limit any microbiological growth, in particular growth of thermophilic flora.

Their temperature resistance also makes it possible to carry out a sterilization before they are brought into service. This sterilization consists in passing steam at 2 bar through the casing for a period of 20 minutes. This sterilization is followed by rinsing with purified water (within the meaning of the pharmacopeia) for a period of 5 minutes.

These filters also have capacities to withstand certain chemical products used for equipment cleaning operations, and in particular peracetic acid at a concentration of 5‰.

An integrity test can be carried out on these cartridges using an integrity test from the company MILLIPORE for example. This integrity test is carried out when the cartridges are installed in order to verify the assembly thereof. This test is then carried out before each cleaning of the equipment and, finally, before the disassembling in order to validate the correct functioning of said cartridges during the production phase.

The working pressure difference (ΔP) of these filters must not exceed 2 bar in order to guarantee their integrity. Should this be the case, these filters must be replaced with new ones.

The third of the four means implemented for purifying the glucose polymers for the production of peritoneal dialysis solutions in accordance with the invention consists in using a heat treatment.

More particularly, a heat treatment of which the time/temperature pair is chosen so as to reduce the bioburden of thermophilic microorganisms capable of contaminating the glucose polymers.

This heat treatment step then consists in heating at a temperature between 100 and 130° C., preferably at a temperature of 120° C., for 1 to 5 minutes, preferably 2 minutes.

This step of treatment at high temperature for a short period of time is altogether different than the hours of heat treatment conventionally carried out in the prior art by boiling a reaction medium in order, for example, to denature proteins (in particular in, order to inactivate enzymes).

The heat treatment according to the invention is carried out by means of a tubular heat exchanger in which the chromatographed starch hydrolyzate circulates, and is surrounded by a calender fed with steam at 2 bar in order to regulate therein a temperature of about 120° C.

This tubular heat exchanger, which is, for example, manufactured by the company ACTINI, consists of several parts:
- a section for recovery of energy produced/produced between the entry and the exit of the zone;
- a section for heating with steam at 2 bar;
- a holding section which is integrated and can be modulated according to the desired residence time.

The length of this heat exchanger is calculated in order to guarantee the desired residence time according to the feed flow rate. For example, the feed flow rate may be between 3000 and 4000 liters/hour for a holding section of about 100 to 130 liters.

This heat treatment allows a reduction of at least 2 log in microorganisms, and in particular acidothermophilic bacteria, of *Alicyclobacillus acidocaldarius* type.

The fourth of the four means implemented for purifying the glucose polymers for the production of peritoneal dialysis solutions in accordance with the invention consists in using an ultrafiltration.

More particularly, the cut-off threshold is chosen so as to retain the possible contaminants in the retentate.

The ultrafiltration membrane then has a cut-off threshold of between 30 000 and 100 000 daltons, preferably of about 50 000 daltons.

The surface area of the filter determines the filtration, capacity of the filter, this surface area being determined according to the nature of the fluid and to the flow rate to be treated.

The cut-off threshold makes it possible to retain the microorganisms, and in particular the acidothermophilic bacteria of *Alicyclobacillus acidocaldarius* type, and also a part of the endotoxins, peptidoglycans and β-glucans, their size being between 1000 and 100 000 daltons.

The ultrafiltration membranes may be of ceramic or organic type. Since these two types of membranes have a different temperature resistance, membranes of ceramic type which make it possible to work at temperatures of above 75° C. will be preferred.

Their temperature resistance makes it possible to carry out a steam sterilization before they are put into service. This sterilization consists in passing steam at 2 bar through the casing for a period of 20 minutes. This sterilization is followed by rinsing with purified water for a period of 20 minutes.

It is thus also advisable to work, at a temperature above 75° C. in order to avoid any microbiological growth.

These filters also have capacities to withstand certain chemical products used for cleaning equipment, and in particular peracetic acid at a concentration of 5‰ and sodium hydroxide at a concentration of 1%.

The feed syrup pressure is between 5 and 10 bar and is regulated by the pump feeding this module. In the case where the maximum pressure is reached but the syrup flow rate is too low, it is advisable to clean the membranes with sodium hydroxide so that said membranes return to full, efficiency.

The monitoring of the decrease in the level of contaminants (endotoxins, peptidoglycans and β-glucans) can be analyzed by periodically taking samples from the filtrate.

This fourth means makes it possible, with the three other means, to guarantee that the presence of any possible contaminant of peptidoglycan, endotoxin and/or β-glucan type in the final product will be at a value below the thresholds defined above.

One of the methods in accordance with the invention that is preferred for obtaining glucose polymers for the preparation of peritoneal dialysis solutions can thus be explained in detail by the succession of the following steps:

1) obtaining a waxy starch milk with a final dry matter content of between 35 and 40%,
2) subjecting the resulting waxy starch milk to acid hydrolysis and, optionally, adding to this acid hydrolysis by means of an enzymatic hydrolysis with bacterial alpha-amylase to give a DE between 9 and 14, preferably between 10 and 13,
3) carrying out, on the resulting starch hydrolyzate, a step of treatment with activated carbon and/or with granular black carbon,
4) implementing a sterilizing filtration consisting of two membrane filtrations where the pore diameter is 0.45 μm then 0.22 μm,
5) chromatographing this hydrolyzate on macroporous strong cationic resins in alkali metal or alkaline-earth metal form;
6) collecting the starch hydrolyzate, more specifically the glucose polymers, excluded during this chromatography step,
7) implementing, on these glucose polymers, a step of heat treatment at a temperature of 120° C. for 2 minutes,
8) carrying out a step of treatment with activated carbon and/or with granular black carbon,
9) implementing a sterilizing filtration consisting of two membrane filtrations where the pore diameter is 0.45 μm then 0.22 μm,
10) carrying out an ultrafiltration with a cut-off threshold of between 30 000 and 100 000 daltons, preferably of about 50 000 daltons.

It appears that this succession of steps makes it possible to increase, step by step, the safety of the obtention of the glucose polymers for the preparation of peritoneal dialysis solutions.

A first step of treatment with activated carbon and/or with granular black carbon is carried out on the starch hydrolyzate.

A sterilizing filtration step is carried out on the starch hydrolyzate treated with activated carbon and/or with granular black carbon, before it is subjected to chromatography.

Finally, the starch hydrolyzate chromatographed undergoes four successive purification steps:
heat treatment,
activated carbon and/or granular black carbon,
sterilizing filtration,
ultrafiltration.

These glucose polymers are then used for preparing the actual peritoneal dialysis solution, In order to guarantee over time the efficiency of the purification method in accordance with the invention, it is chosen to perform regular cleaning of the equipment used for said purification of the glucose polymers.

This method is then characterized in that the following are carried out:
a) after the production of the 4$^{th}$ batch of final product, a first cleaning operation which consists of:
at least one step of washing with water in order to remove the glucose polymer,
at least one disinfecting step, and
at least one step of rinsing with purified water;
b) after the production of the 12$^{th}$ batch of final product, a second cleaning operation which consists of:
at least one step of washing with water in order to remove the glucose polymer,
at least one detergency step,
at least one step of rinsing with water,
at least one disinfecting step, and
at least one step of rinsing with purified water.

The step of washing with water in order to remove the glucose polymer is applied until a refractometer reading measurement of less than 0.5 is obtained.

The disinfecting step consists of a treatment with peracetic acid diluted to 0.05% for at least 10 minutes, or consists of a steam treatment at a pressure of 2 bar for at least 20 minutes.

The detergency step consists of a treatment with sodium hydroxide diluted to 1% for at least 30 minutes.

The step of rinsing with purified water is applied for at least 5 minutes.

The invention will be understood more clearly by means of the examples which follow, which are meant to be illustrative and nonlimiting.

EXAMPLE 1

The starting material for obtaining the glucose polymers according to the invention is produced from waxy corn starch in the following way:
cleaning of the corn so as to keep exclusively the whole corn grains,
steeping of the corn thus cleaned, in the presence of lactic acid so as to soften the grains,
wet milling, then separation of the various constituents, i.e. germ, cellulose husk, proteins and starch,
cleaning of the starch in countercurrent mode with sanitized water so as to purify the starch both physicochemically and bacteriologically,
centrifugation and drying of the starch,
suspension of the starch in sanitized water at a final dry matter content of 40% and at a temperature of from 45° C. to 50° C.,
acidification of the starch suspension by addition of HCl at a pH <2, and raising of the temperature to 115 to 120° C. for 6 to 8 minutes,
flocculation of the proteins and of the fats at this pH,
neutralization of the suspension at pH 5,
filtration of the suspension through diatomaceous earth (so as to retain the residual proteins, fats and cellulose),
demineralization on strong cationic resin and weak anionic resin,
treatment with activated carbon at a temperature of 70-80° C. and at a pH of from 4 to 4.5; which removes the colored impurities and, reduces the level, of microbiological impurities.

The activated carbon powder which is added at a concentration between 0.2 and 0.5% on a dry basis is retained on a 10 μm ceramic filter loaded beforehand with a filtering agent,
concentration by passing through a falling film evaporator,
spray-drying of the concentrated solution in an MSD spray dryer sold by the company NIRO.

This starch hydrolyzate complies with the monograph of the European pharmacopeia (ref Maltodextrins: 1542).
pH: 4.0-7.0 for a solution at 10%,
i.d.: complies,
loss on drying: 6% max
DE: <20
Sulfated ash: 0.5% max
$SO_2$: 20 ppm max
Heavy metals: <10 ppm
E. coli: absent/g
Salmonellae: absent/10 g
Total viable microorganisms: 100 CFU/g max (EP 1000 CFU/g)
Molds: 100 CFU/g max In addition to this, the batches produced are analyzed on the basis of the values of:

yeast+mold contamination: 150 CFU/10 g max, i.e. 15/g max aerobic microorganisms: 500 CFU/10 g max, i.e. 50/g max endotoxins (endpoint gel clot LAL test): 20 EU/g max peptidoglycans: (validated SLP-HS test): 2700 ng/g max.

The conditions for obtaining the glucose polymers in accordance with the invention from the starch hydrolyzate thus obtained are the following:

1) water preparation/water quality purification of the water by filtration through 3 μm; treatment on activated carbon, demineralization on cation and anion exchange resins, and filtration again (UA), two tanks used:

10 m³ for dissolving the starch hydrolyzate, and the spray-dryer rinsing and cleaning steps, 60 m³ for the main process (cleaning of the tanks, its suspensions of activated carbon and chromatography).

2) Chromatography solubilization of the starch hydrolyzate with purified water so as to obtain a dry matter content of 35-45% at a temperature between 60-85° C., sterilizing filtration of the starch hydrolyzate by passing it through 0.45 μm and then 0.22 μm, carried out at a ΔP <3 bar, size exclusion chromatography (SEC) separation carried out using a continuous system composed of 6 series of double plates, each of 1 m³ of resin. The resin used is a PCR145K sold by the company Purolite®.

The solution which passes through this resin has a temperature between 75 and 85° C. at 35-45% dry matter content.

The duration of each sequence defines the process.

In the present case, the duration of each sequence is 15 minutes.

The control is carried out by analysis of molecular weight distribution and analysis of the chromatography yield, in the following way: (amount of dry matter of the desired fraction)/(amount of dry matter of the feed).

The lowest molecular weights interact with the resin and the high molecular weights are eluted with purified water;

concentration is carried out by falling film evaporation at a dry matter content of 35-45%;

a heat treatment is carried out at a temperature of 120° C. for 2 minutes;

activated carbon is added between 0.5 and 1.5% of the total weight of the starch hydrolyzate at 75° C. with cationic resins (1 to 3 l) for controlling the pH (4-4.5) and anionic resins (5 to 10 l) for controlling the pH (5.5-6);

filtration carried out through polypropylene bag filters with ΔP <5 bar, in 5 to 6 hours per batch;

second and third filtrations through 1.5 and 0.45 μm are then carried out;

then through 0.22 and 0.1 μm, ultrafiltration through a membrane with a cut-off threshold of about 40 000 Da.

For the spray-drying: feed at 500 kgs/h with a solution at 40% dry matter content and at 250° C. in an MSD spray-dryer sold by the company Niro.

The spray-dried product has, on exiting, a moisture content of less than 6%.

The product is then cooled in a fluidized airbed comprising 3 cooling zones fed with air at 40, 30 and 20° C. The product obtained is then sieved through 800 μm in order to remove the aggregates.

About 500 kgs of final product are obtained from 800 kgs of starting maltodextrins, i.e. a yield of about 60%.

The determination of the possible contamination of the circuit is carried out by analysis of the peptidoglycan and endotoxin content on the final product.

For example, the contents usually observed and measured on the batches of the final product (expressed per g of glucose polymer) are, for the criteria specified above, the following:

Yeast and molds: 0/g

Aerobic microorganisms: 0/g

Endotoxins (endpoint gel clot LAL test): 0.3 EU/g

Peptidoglycans (validated SLP-HS test): <3 ng/g

*B. acidocaidarius:* 1/g

EXAMPLE 2

It was decided to test the efficiency of the method for purifying glucose polymers for the production of peritoneal dialysis solutions, in accordance with the invention (i.e. characterized by the implementation of each of the four treatment steps), compared with a method of purification using only two or even three of the four steps of the method in accordance with the invention (a step of treatment with activated carbon and a sterilizing filtration step in a first scenario, a step of treatment with activated carbon, a sterilizing filtration step and a heat treatment step in a second scenario).

1) Implementation of the Purification Method in Two Steps:

The details of the operating conditions are those defined in example 1, with the exception of the heat treatment and ultrafiltration steps not used in this first case.

A batch "A" of glucose polymers is chosen, the microbiological analyses of which gave the following results:

Yeasts and molds: <50/10 g

Aerobic microorganisms: 50/10 g

Endotoxins: 19 EU/g (endpoint gel clot LAL test)

Peptidoglycans: 1520 ng/g (validated SLP-HS test)

*B. acidocaldarius:* 1/g

This method uses powdered activated carbon of the NORIT SX+ brand at 0.65% dry/dry and the treatment is applied for a contact time of one hour.

A sterilizing filtration step is then applied with cartridge filters in series, sold by the company MILLIPORE, of 0.45 μm and 0.22 μm.

The final product "B" then exhibits the following microbiological results:

Yeasts and molds: 0/g

Aerobic microorganisms: 0/g

Endotoxins: <0.3 EU/g (endpoint gel clot LAL test)

Peptidoglycans: 47 ng/g (validated SLP-HS test)

*B. acidocaidarius:* 0/g

2) Implementation of the Purification Method in Three Steps

The following operating conditions are applied to the final product "B":

preparation of a solution at 10% of dry matter content with purified water, heat treatment at 120° C. for 2 minutes, concentration to 30% dry matter content.

The final product "C" then exhibits the following microbiological results:

Yeasts and molds: 0/g

Aerobic microorganisms: 0/g

Endotoxins: <0.3 EU/g (endpoint gel clot LAL test)

Peptidoglycans: <20 ng/g (validated SLP-HS test)

*B. acidocaldarius:* 0/g

3) Implementation of the Purification Method in Accordance with the Invention

The following operating conditions are applied to the final product "C":
- ultrafiltration through a membrane with a cut-off threshold of 40 000 daltons.

The final product "D" then exhibits the following microbiological results:
Yeasts and molds: 0/g
Aerobic microorganisms: 0/g
Endotoxins: <0.3 EU/g (endpoint gel clot LAL test)
Peptidoglycans: <3 ng/g (validated SLP-HS test)
*B. acidocaldarius:* 0/g It is clearly apparent that the purification method in accordance with the invention makes it possible to guarantee a remarkably low peptidoglycan contaminant level; the purification method in two steps and in three steps does not make it possible, starting from the batch "A", to recover a glucose polymer having even a peptidoglycan contaminant level less than the threshold value of 8 ng/g that would permit the use thereof in peritoneal dialysis.

It is thus proved that, even if one of the batches of glucose polymers happen to be found to be abnormally loaded with peptidoglycans, the purification method in accordance with the invention would make it possible to efficiently reduce the content thereof, thus guaranteeing a contamination content well below the limit of tolerance commonly accepted.

EXAMPLE 3

In order to guarantee the quality of the circuits used, regular washing of the equipment is carried out in the following way.

The cleaning of a tank for dissolving raw material (starch hydrolyzate) is selected here.

After use of this tank for the production of 12 batches of final product, the following sequences are applied:
- washing with water by means of a clean-in-place (CIP) system in order to remove any trace of product (starch hydrolyzate).

The efficiency of this washing is tested by means of a refractometer reading (RR) measurement on the washing waters leaving this tank (RR<0.5);
- introduction of sodium hydroxide from the manufacturer Solvay at 1% by means of the same CIP system for 30 minutes;
- rinsing with water in order to remove the traces of sodium hydroxide. The efficiency of this rinsing is tested by means of a pH measurement on the rinsing waters leaving this tank;
- introduction of Bactipal peracetic acid from the company SEPPIC, diluted to 0.05%, by means of the same CIP system for 10 minutes;
- rinsing with purified, water in order to remove the traces of acid. The efficiency of this rinsing is tested by means of a peroxide test on the rinsing waters leaving this tank.

The invention claimed is:

1. A method for purifying glucose polymers for the production of a peritoneal dialysis solution, wherein the glucose polymer has dextrose equivalent (DE) of 9 to 14, the method comprising:
 - at least one step of contacting a solution comprising glucose polymers with activated carbon and/or with granular black carbon, wherein the treatment with activated carbon and/or with granular black carbon comprises a first stage composed of activated carbon and a second stage composed of activated carbon or of granular black carbon,
 - at least one sterilizing filtration step for said solution, wherein the sterilizing filtration step comprises two membrane filtration steps, a first membrane filtration step through a sterilization filter having a pore diameter of 0.45 µm followed by a second membrane filtration step through a sterilization filter having a pore diameter of 0.22 µm,
 - at least one heat treatment step for said solution, wherein the heat treatment step comprises heating at a temperature of between 100 and 130° C. for 1 to 5 minutes, and
 - at least one ultrafiltration step for said solution, wherein the ultrafiltration membrane has a cut-off threshold of between 30,000 and 100,000 Daltons to form a peritoneal dialysis solution free from endotoxins, peptidoglycans and β-glucans.

2. The method according to claim 1, wherein the glucose polymer is icodextrin.

3. The method according to claim 1, wherein the glucose polymer contains less than 3% glucose and of glucose polymers having a degree of polymerization (DP) less than or equal to 3.

4. A method for purifying glucose polymers for the production of a peritoneal dialysis solution, wherein the glucose polymer has DE of 9 to 14, said method comprising:
 a) obtaining a waxy starch milk with a final dry matter content of between 35 and 40%,
 b) subjecting the waxy starch milk to acid hydrolysis and, optionally, enzymatic hydrolysis with bacterial alpha-amylase to provide a starch hydrolysate having a DE between 9 and 14,
 c) contacting the starch hydrolysate with activated carbon and/or with granular black carbon,
 d) a sterilization step of the hydrolysate of step c) comprising membrane filtration through a sterilization filter having a pore diameter of 0.45 µm followed by membrane filtration through a sterilization filter having a pore diameter of 0.22 µm,
 e) chromatography of the sterilized hydrolysate on macroporous strong cationic resins in alkali metal or alkaline-earth metal form;
 f) collecting glucose polymers excluded during the chromatography step,
 g) treating the glucose polymers with heat at a temperature of 120° C. for 2 minutes,
 h) contacting the heat treated glucose polymer solution with activated carbon and/or with granular black carbon,
 i) a sterilization step of the glucose polymer solution of step h) comprising membrane filtration through a sterilization filter having a pore diameter of 0.45 µm followed by membrane filtration through a sterilization filter having a pore diameter of 0.22 µm, and
 j) ultrafiltration of said sterilized glucose polymer solution in an ultrafiltration system having a cut-off threshold of between 30,000 and 100,000 Daltons to form a peritoneal dialysis solution free from endotoxins, peptidoglycans and β-glucans.

5. The method according to claim 4, wherein the glucose polymer is icodextrin.

6. The method according to claim 4, wherein the glucose polymer contains less than 3% glucose and of glucose polymers having a degree of polymerization (DP) less than or equal to 3.

* * * * *